(12) United States Patent
Morningstar (10) Patent No.: US 7,160,325 B2
(45) Date of Patent: Jan. 9, 2007

(54) IMPLANTABLE MEDICAL BALLOON AND VALVE

(75) Inventor: Randy L. Morningstar, Brooklyn Park, MN (US)

(73) Assignee: AMS Research Corporation, Minnetonka, MN (US)

( * ) Notice: Subject to any disclaimer, the term of this patent is extended or adjusted under 35 U.S.C. 154(b) by 894 days.

(21) Appl. No.: 09/872,704

(22) Filed: Jun. 1, 2001

(65) Prior Publication Data

US 2002/0173698 A1 Nov. 21, 2002

Related U.S. Application Data

(60) Provisional application No. 60/291,493, filed on May 15, 2001.

(51) Int. Cl.
*A61F 2/02* (2006.01)
*A61F 2/04* (2006.01)

(52) U.S. Cl. .................. 623/11.11; 623/23.66

(58) Field of Classification Search .......... 600/29, 600/30, 31, 32; 604/96.01, 99.02, 99.03, 604/99.04, 907, 921, 96, 103, 164.01, 99.01; 251/903; 152/427; 473/611; 623/11.11, 623/7, 8, 23.66, 23.67, 23.68; 606/190–195
See application file for complete search history.

(56) References Cited

U.S. PATENT DOCUMENTS

| | | | |
|---|---|---|---|
| 2,513,014 A | 6/1950 | Fields | |
| 2,731,028 A * | 1/1956 | McCord | 137/223 |
| 2,856,920 A | 10/1958 | Indelicato | |
| 3,768,102 A * | 10/1973 | Kwan-Gett et al. | 623/23.66 |
| 3,795,246 A | 3/1974 | Sturgeon | |
| 3,831,585 A | 8/1974 | Brondy et al. | |
| 3,834,394 A | 9/1974 | Hunter et al. | |
| 4,019,499 A | 4/1977 | Fitzgerald | |
| 4,102,342 A * | 7/1978 | Akiyama et al. | 606/192 |
| 4,213,461 A | 7/1980 | Pevsner | |
| 4,240,433 A | 12/1980 | Bordow | |
| 4,240,630 A * | 12/1980 | Hoffman | 473/610 |
| 4,282,875 A | 8/1981 | Serbinenko et al. | |
| 4,311,146 A | 1/1982 | Wonder | |

(Continued)

FOREIGN PATENT DOCUMENTS

EP 0 200 286 A2 11/1986

(Continued)

OTHER PUBLICATIONS

UroVive, Transurethral Delivery System—Clinician Directions for use, UroSurge.

(Continued)

*Primary Examiner*—Henry Bennett
(74) *Attorney, Agent, or Firm*—Jose' W. Jimenez; Kimberly K. Baxter (57) ABSTRACT

A medical balloon, implantable in human tissue, of unitary silicone construction. The balloon is self-sealing upon removal of an inflation implement. The balloon device comprises a molded valve portion which is dip-coated in a silicone dispersion to create a balloon wall around and integral with the valve portion. Preferably, both the valve portion and the balloon wall are comprised of the same silicone material. The dipping process, combined with a vulcanizing process, creates a laminar wall which is strong and resistant to separation during inflation. The balloons may be used in for the treatement of urinary incontinence or vesicoureteral reflux, alternative procedures such as emboliztion or blocking of veins or arteries to accomplish the treatement of enlarged blood vessels in the brain or for treating severe uterine bleeding.

29 Claims, 3 Drawing Sheets

U.S. PATENT DOCUMENTS

| | | | |
|---|---|---|---|
| 4,327,734 A | 5/1982 | White, Jr. | |
| 4,327,912 A * | 5/1982 | Hoffman | 473/606 |
| 4,334,327 A | 6/1982 | Lyman et al. | |
| 4,341,218 A * | 7/1982 | U | 606/195 |
| 4,346,712 A | 8/1982 | Handa et al. | |
| 4,364,392 A * | 12/1982 | Strother et al. | 606/195 |
| 4,395,806 A | 8/1983 | Wonder et al. | |
| 4,402,319 A | 9/1983 | Handa et al. | |
| 4,429,724 A | 2/1984 | Dorros et al. | |
| 4,441,495 A * | 4/1984 | Hicswa | 606/195 |
| 4,479,649 A * | 10/1984 | Newcomb et al. | 473/570 |
| 4,497,074 A * | 2/1985 | Rey et al. | 623/124 |
| 4,517,979 A * | 5/1985 | Pecenka | 606/195 |
| 4,520,823 A | 6/1985 | LeVeen et al. | |
| 4,545,367 A * | 10/1985 | Tucci | 128/898 |
| 4,557,255 A | 12/1985 | Goodman | |
| 4,559,043 A | 12/1985 | Whitehouse et al. | |
| RE32,348 E * | 2/1987 | Pevsner | 606/194 |
| 4,686,962 A | 8/1987 | Haber | |
| 4,697,584 A * | 10/1987 | Haynes | 606/95 |
| 4,773,393 A | 9/1988 | Haber et al. | |
| 4,802,479 A | 2/1989 | Haber et al. | |
| 4,819,637 A * | 4/1989 | Dormandy et al. | 606/195 |
| 4,826,501 A * | 5/1989 | Grundei | 623/8 |
| 4,832,680 A | 5/1989 | Haber et al. | |
| 5,002,556 A | 3/1991 | Ishida et al. | |
| 5,007,898 A | 4/1991 | Rosenbluth et al. | |
| 5,064,434 A | 11/1991 | Haber | |
| 5,071,429 A | 12/1991 | Pinchuk et al. | |
| 5,078,681 A | 1/1992 | Kawashima | |
| 5,108,430 A * | 4/1992 | Ravo | 623/23.68 |
| 5,181,921 A | 1/1993 | Makita et al. | |
| 5,222,970 A | 6/1993 | Reeves | |
| 5,304,123 A | 4/1994 | Atala et al. | |
| 5,358,001 A * | 10/1994 | Smith | 137/223 |
| 5,411,475 A | 5/1995 | Atala et al. | |
| 5,558,829 A * | 9/1996 | Petrick | 264/263 |
| 5,624,395 A * | 4/1997 | Mikhail et al. | 604/99.04 |
| 5,720,734 A * | 2/1998 | Copenhaver et al. | 604/247 |
| 5,830,228 A | 11/1998 | Knapp et al. | |
| 5,876,375 A | 3/1999 | Penny | |
| 5,934,310 A * | 8/1999 | Littlehorn | 137/223 |
| 5,935,164 A | 8/1999 | Iversen | |
| 5,964,806 A | 10/1999 | Cook et al. | |
| 6,050,934 A * | 4/2000 | Mikhail et al. | 600/30 |
| 6,293,923 B1 * | 9/2001 | Yachia et al. | 604/96.01 |
| 6,312,405 B1 * | 11/2001 | Meyer et al. | 604/96.01 |
| 6,379,329 B1 * | 4/2002 | Naglreiter et al. | 604/99.02 |
| 6,520,977 B1 * | 2/2003 | Piraka | 606/193 |
| 2003/0004534 A1 | 1/2003 | George et al. | |
| 2004/0267378 A1 * | 12/2004 | Gazi et al. | 623/23.67 |

FOREIGN PATENT DOCUMENTS

| | | |
|---|---|---|
| EP | 0 458 649 A1 | 11/1991 |
| WO | WO 88/00070 | 1/1988 |
| WO | WO 89/00030 | 1/1989 |
| WO | WO 93/07815 | 4/1993 |
| WO | WO 99/60932 | 12/1999 |
| WO | WO 00 54701 | 9/2000 |

OTHER PUBLICATIONS

UroVive, Periurethral Delivery System—Clinician Directions for use, UroSurge.

UroVive, Self Contained Microballoon System—Clinician Directions for use, UroSurge.

* cited by examiner

IMPLANTABLE MEDICAL BALLOON AND VALVE

CROSS REFERENCE TO RELATED APPLICATIONS

This application claims priority to U.S. provisional patent application No. 60/291,493, filed May 15, 2001 which is incorporated by reference herein.

BACKGROUND OF THE INVENTION

The present invention pertains generally to an implantable microballoon and a method of making such a microballoon.

Implantable microballoons provide a minimally invasive treatment for the urological condition of stress urinary incontinence resulting from Intrinsic Sphincter Deficiency (ISD). Treatment of the condition is completed through placement of one or more implantable balloons into the periurethral tissue of the bladder neck. Implantation of the balloons results in the coaptation of the urethra which improves or resolves the incontinence condition.

Delivery is completed by insertion of the microballoon into the tissue parallel to the urethra. The microballoon is then inflated and left in the bladder neck.

Microballoons can be similarly used for the treatment of vesicoureteral reflux (VUR—reflux of the urine from the bladder up the urethras to the kidneys) and alternative procedures such as embolization or blocking of veins or arteries to accomplish the treatment of enlarged blood vessels in the brain or for treating severe uterine bleeding. Slightly larger balloons may be used for fecal incontinence or gastrointestinal reflux.

Until now, the small size and numerous intricacies of microballoons have presented problems pertaining to performance and manufacture. The valves that are included in such microballoons are typically constructed using numerous parts and designed to be self-sealing once an inflation syringe is removed therefrom. In the assembled condition, an outsidewall of the valve is typically attached to the inside neck of a microballoon using adhesive or similar bonding procedure.

Such a manufacturing method is laborious and expensive. Moreover, when the balloons are inflated, there is a tendency for the adhesive to fatigue, separate and allow the fluid contained within the balloon chamber to leak. Even when the adhesive holds, however, the valve can leak due to manufacturing defects that can result from the complexity and size of the valve.

In view of the above, there is a need for a valve which is simple, reliable and relatively inexpensive. There is also a need for a method of manufacturing a microballoon which is repeatable, efficient, and relatively simple.

BRIEF SUMMARY OF THE INVENTION

Provided is a microballoon which is relatively simple in construction and manufacture and provides an increased level of reliability and cost efficiency. The microballoon generally comprises a valve portion of unitary construction, which is a molded valve body made of a material, such as silicone, capable of being punctured and resealed. The valve portion includes a cylindrical wall extending therefrom having an open end which is constructed and arranged such that when the open end is dipped into a solution of material, such as silicone, a meniscus forms over the end.

When the meniscus solidifies, it closes the end of the cylindrical wall, thereby creating a completely enclosed inner chamber. The valve portion is then dipped into the solution again and allowed to solidify in order to form another layer over substantially the entire valve portion. This process is repeated until the cylindrical wall is built up to a desired thickness, thereby creating the microballoon.

This method obviates the need for adhesives to bond the valve portion to the inner wall of a microballoon. Rather, the microballoon and the valve are integral and problems pertaining to separation between the valve portion and the balloon portion are avoided.

Additionally, the repeated dipping creates multiple layers of material in the formation of the balloon. Such a "laminate" balloon wall is significantly stronger than a wall formed in a single step.

Moreover, this method of manufacturing a microballoon is much simpler than conventional methods which require assembling intricate valve portions using a plurality of separate parts and subsequently adhering the valve portion to the balloon portion. The balloon designs and methods of manufacture of the present invention are also effective for creating balloons of various sizes.

Once the balloon is created, a piercing is placed through the valve body using a needle like instrument. This piercing defines a path through which an inflation member may be inserted without imparting damage to the valve body. Preferably, this piercing has a curved portion which improves the sealing characteristic of the piercing when subjected to back pressure, such as that created by the inflated balloon. This curved portion is created by bending the balloon midway through the piercing operation.

The term "piercing" is used to describe the channel created through the valve body and stem which remains substantially collapsed or closed unless forced open by an implement which is substantially rigid, relative to the soft material of the valve body. Though the piercing is created by piercing the valve body with a sharp, needle-like instrument, it is understood that the piercing could be created using other methods such as molding or the like. For example, if a threadlike sacrificial strand is held in place while the valve body is being molded, and pulled out and discarded once the body set, such a "piercing" would likely form and perform adequately. Due to the resiliency of the material used, however, best results are likely to be obtained by actually piercing the valve body with a fine, needle-like implement.

BRIEF DESCRIPTION OF THE DRAWINGS

FIGS. 4A, 4B, 4C, 4D, 41E and 4F are a series of sectional views of the device of the present invention in progressive stages of manufacture.

DETAILED DESCRIPTION OF THE INVENTION

Figure 1:
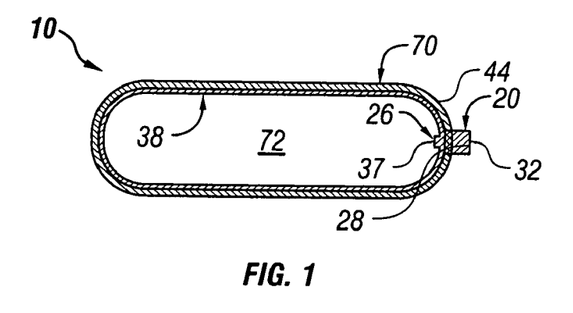
FIG. 1 is a sectional view of the device of the present invention in an inflated state.

Referring now to the Figures, and first to FIG. 1, there is shown a completed device 10 of the present invention in an inflated state. Device 10 generally comprises a valve portion 20 and a balloon portion 70.

Figure 2:
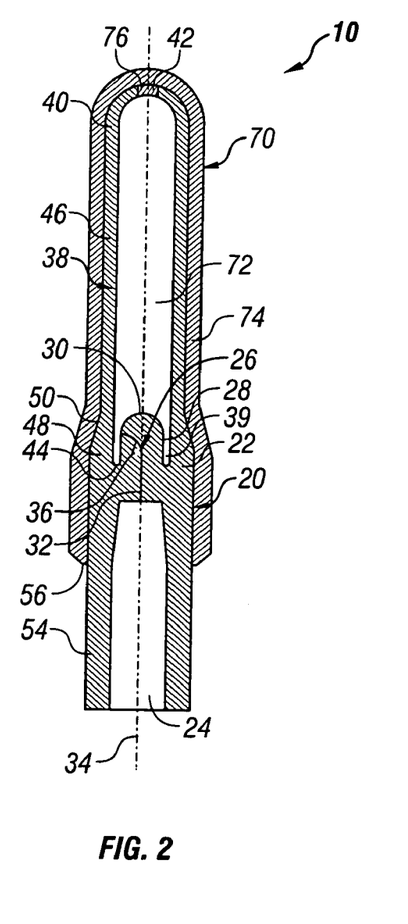
FIG. 2 is a sectional view of the device of the present invention in a deflated state.

FIG. 2 provides a detailed depiction of the device 10 in a deflated state and prior to its first inflation. The valve portion 20 is of unitary construction and includes a valve body 22 and a valve stem 26. The valve body 22 is preferably cylindrical and defines an inlet 24 in its lower side. The inlet 24 is cylindrical, frustoconical, conical, semispherical, or a similar suitable shape, and substantially concentric with the valve body 22.

The valve stem 26 is integral with the valve body 22 and extends upwardly therefrom, opposite the inlet 24. The valve stem 26 has at least one side 28 and a tip 30. Preferably, the valve stem 26 is cylindrical and the tip 30 is rounded, thereby forming somewhat of a silo shape. The valve stem 26 is substantially concentric with the valve body 22 and the inlet 24. It has an outside diameter which is smaller than the diameter of the body 22. When the valve portion 20 is operably attached to the balloon portion 70, the valve stem 26 extends into an inner chamber 72 of the balloon portion 70.

The valve portion 20 is preferably molded from an elastomeric or similarly resilient material such as silicone. Such a material is advantageous because it can be pierced and remain fluid-tight after removing the piercing implement. Thus, a channel or piercing 32 is defined by the valve portion 20 and provides a path for a rigid inflation tube to follow when inserted into the balloon, thereby preventing the valve portion 20 from being damaged by the insertion of an inflation tube during an implantation operation. The piercing 32 leads from the inlet 24 to the inner chamber 72 through the valve body 22 and the valve stem 26. Preferably, the piercing 32 begins in the inlet 24 along a longitudinal axis 34, which is shared by the inlet 24, the valve body 22, and the valve stem 26. The piercing 32 continues along this longitudinal axis 34 until it reaches a predetermined location in the valve stem 26 where a curved portion or bend 36 is formed in the piercing 32, such that the piercing 32 exits the side 28 of the valve stem 26. The bend 36 is advantageous in that it enhances the ability of the silicone to close the piercing 32, thereby making the chamber 72 fluid-tight when the piercing 32 is not held open by a substantially rigid member. A close look at FIG. 1 shows how the valve stem 26 stretches and flattens during inflation. It can be seen that bend 36 of the piercing 32 forms somewhat of a flap 37 which is held closed by the pressure contained within the inner chamber 72.

A cylindrical sidewall 38 extends upwardly from the valve body 22 in a direction substantially parallel to that of the valve stem 26. The cylindrical sidewall is laterally or radially displaced from the valve stem 26 and is substantially concentric therewith. The sidewall 38 has an inner diameter which is greater than an outer diameter of the valve stem 26, thereby creating an annular space 39 between the valve stem 26 and the sidewall 38.

The annular space 39 created between the valve stem 26 and the sidewall 38 is defined on its lower side by a curved portion or web 44. Web 44 is concave and opens upwardly toward the inner chamber 72 of the balloon portion 70. Web 44 functions to relieve stress from the union of the valve body 22 and the cylindrical sidewall 38 when the device 10 is inflated. Web 44 is also shaped to ease the molding process of the valve body 22.

Referring briefly back to FIG. 1, it can be seen how the annular space 39 virtually disappears when the valve portion 20 stretches due to inflation. The web 44 creates a smooth transition between the sidewall 38 and the side 28 of the valve stem 26. It can also be seen that the elastic properties of the cylindrical sidewall 38 and the balloon wall 74 are similar if not identical, acting in concert while stretching and forming the desired balloon shape.

Referring again to FIG. 2, an end portion 40 extends upwardly from the sidewall 38 and bends inwardly to define an opening 42. Although the present invention may be practiced without the inwardly curving end portion 40, it will be seen that the end portion 40 is advantageous in forming a meniscus 76 when the end portion 40 is inverted and dipped in a solution of silicone. This process will be described in more detail below. The opening 42 thus has an inner diameter which is less than an inner diameter of the cylindrical sidewall 38.

Preferably, the outer surface of the cylindrical sidewall 38 comprises an upper sidewall 46 and a lower sidewall 48 connected by a taper 50. Lower sidewall 48 has a greater outer diameter than upper sidewall 46. The function of this taper 50 will become evident when the manufacturing method is described below.

For purposes of manufacture, a skirt 54 is provided that extends downwardly from the valve body 22. The skirt 54, preferably, has an outer diameter that is smaller than outer diameter of the valve body 22. The skirt 54 provides an attachment area so that the valve body 22 may be more readily handled during manufacturing. The smaller outer diameter of the skirt 54 creates a ridge 56 which is used to provide a visual and tactile definition of a lower extent of the valve body 22 and an upper extent of the valve skirt 54 such that the skirt 54 may be removed without removing any material from the valve body 22. The ridge 56 also creates a stop in the event that a dipping mandrel 80 (e.g. FIGS. 4C and 4D) is used to manufacture the device 10. The mandrel 80 is preferably sized such that the skirt 54 frictionally fits within an open end of the mandrel 80. The valve body 22, however, is too large to fit within the mandrel 80. The use of the mandrel 80 will be explained in more detail below.

The device 10 is completed when the balloon portion 70 is attached to, or more specifically formed on, the valve portion 20. The balloon portion 70 comprises a balloon wall 74 which is preferably integral with the cylindrical sidewall 38. The balloon wall 74 begins at approximately the ridge 56 and extends all the way over the end portion 40 and also over the opening 42. Additionally, the balloon portion includes a meniscus plug 76 which fills in the opening 42 and prevents liquid silicone solution from entering the inner chamber 72 during the dipping procedure. Once the balloon portion 70 is attached to the valve portion 20, the inner chamber 72 is defined by the cylindrical sidewall 38, the meniscus plug 76, the valve stem 26, and the web 44.

In a preferred embodiment, the material used to create the balloon wall 74 is the same as the material used to mold the valve portion 20. Once the balloon portion is attached to the valve portion, the distinction between the balloon wall 74 and the cylindrical sidewall 38 disappears and an integral wall of unitary construction is created.

Figure 3:
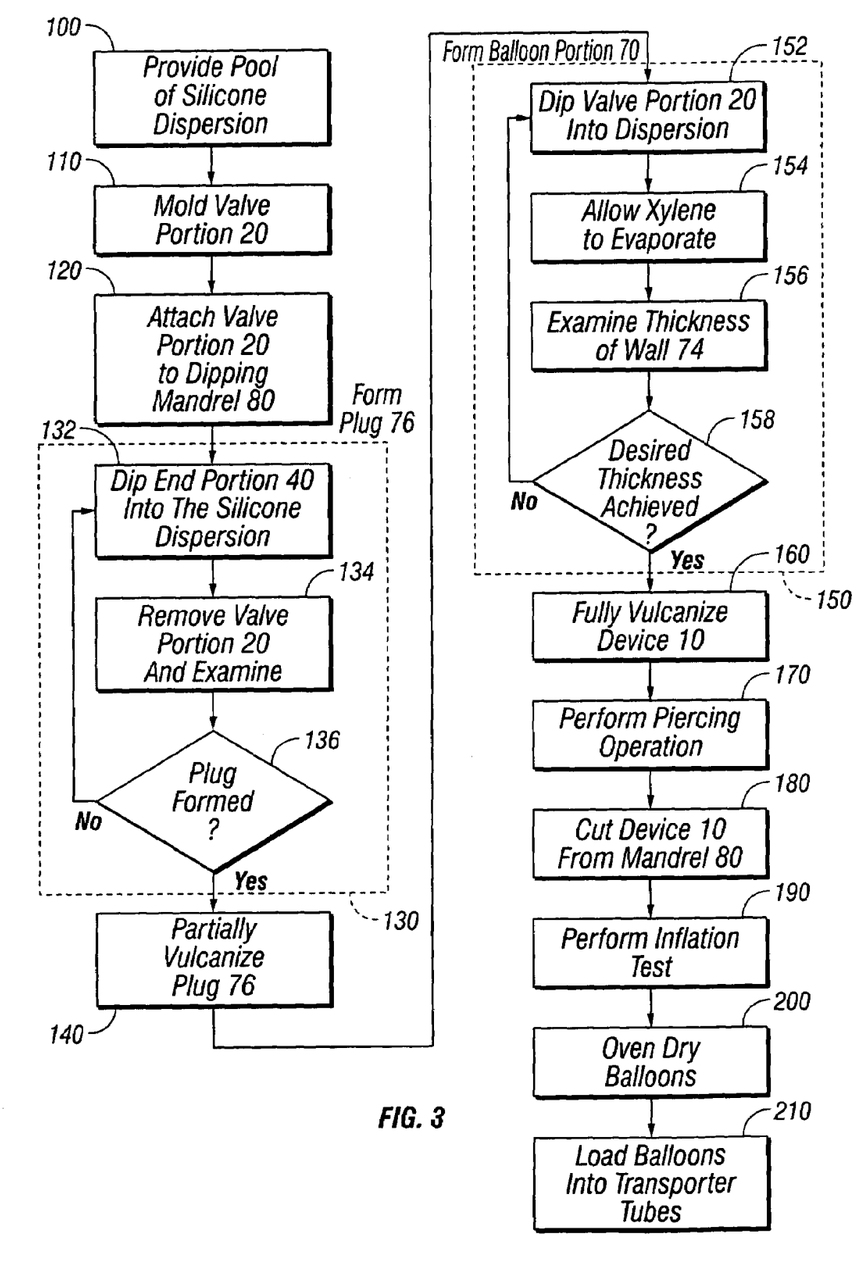
FIG. 3 is a flow chart of a preferred method of the present invention.

Attention is now drawn to FIGS. 3 and 4, which pertain to preferred methods of manufacturing the device 10 of the present invention. FIG. 3 provides a flowchart depicting the steps of a preferred method. FIG. 4 shows the device 10 of the present invention in various states of construction in accordance with the method of FIG. 3.

At 100 (FIG. 3), a silicone dispersion is prepared and placed in a container having sufficient depth to provide a dipping pool into which a valve portion 20, or many valve portions 20, may be dipped. In a preferred embodiment, the dispersion is comprised of a solid silicone gum base or silicone paste mixed with xylene, which breaks down the intermolecular bonds of the solid silicone to form a selfleveling liquid dispersion. The dispersion should be thin enough to form a thin film across the opening 42 when the end portion 40 of the valve portion 20 is dipped into the dispersion. A large opening 42 may require a thicker dispersion than a smaller opening 42. The dispersion becomes thinner as more xylene is used, as is understood by those skilled in the art.

Figure 4A:
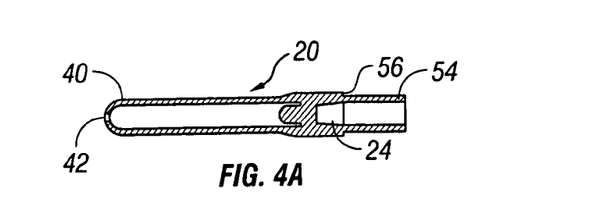

At 110, the valve portion 20 is molded. This may be done in a separate operation or the silicone dispersion from 100 may be used. Preferably the material used to mold the valve portion is the same as the material in the silicone dispersion. FIG. 4A shows a completed valve portion 20. Notably, opening 42 in the end portion 40 of the valve portion 20 is formed by the mold member used to create the contours of the valve stem 26 and web 44, and allows the mold member to be removed therethrough.

Figure 4B:
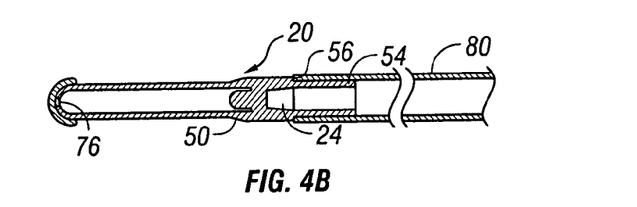

At 120, the molded valve portion 20 is attached to a dipping mandrel or tube 80, as shown in FIG. 4B. The valve portion 20 is attached to the dipping mandrel 80 by inserting the skirt 54 into an open end of the dipping mandrel 80. The skirt 54 is sized to frictionally fit within the opening of the mandrel 80 with enough resistance to movement to prevent the valve portion 20 from falling out of the dipping mandrel 80 when the mandrel 80 is inverted during the dipping operations. The use of a dipping mandrel 80 is preferred because several dipping mandrels 80 may be arranged in close proximity such that the dipping process can occur for several valve portions 20 at once. Other instruments to retain the skirt 54 would be acceptable, especially when the devices 10 are being constructed on an individual basis. Similarly, a dipping mandrel could be constructed and arranged to frictionally fit within the inlet and achieve similar results. FIG. 4B shows the skirt 54 of valve portion 20 inserted within an open end of dipping mandrel 80. Notably, the skirt 54 is inserted until the ridge 56 abuts against the end of the dipping mandrel or tube 80.

The valve portion 20 is now ready for the dipping process used to create the balloon portion 70. At 130 (FIG. 3), the meniscus plug 76 (FIG. 4B) is formed. Forming the meniscus plug 76 comprises inverting the valve portion 20 and dipping mandrel 80 and submerging the end portion 40 of the valve portion 20 into the silicone dispersion at 132. The end portion 40 is submerged deeply enough to ensure that the entire opening 42 comes into contact with the silicone. The valve portion 20 is then removed from the dispersion pool at 134 and held in an inverted position above the dispersion while some of the xylene forming the meniscus 76 has a chance to evaporate, thereby somewhat solidifying the meniscus. The steps of dipping the valve portion and holding it above the dispersion pool are repeated until a plug 76 is formed at 136. Determining the optimal number of times to repeat the process may require a visual inspection, at 134, on the first plug 76 of a batch. It is important that the meniscus plug 76 is thick enough and strong enough to prevent the liquid silicone from entering the inner chamber 72 when the valve portion 20 is later fully dipped in the silicone dispersion in order to form the balloon portion 70. One skilled in the art will see that there are a number of variables which may change the drying time or the number of cycles required to achieve a desired meniscus plug 76. The factors include, but may not be limited to, the size of the opening 42, the thickness of the end portion 40, the length of the cylindrical sidewall 38, the viscosity of the silicone dispersion, and the material used in creating the valve portion 20. It has been found, however, that three to four cycles usually forms an adequate plug 76.

Once the plug 76 has been formed at 130, the plug 76 is partially vulcanized at 140 in order to expel the xylene from the plug 76, thereby solidifying the entire end portion 40. Partial vulcanization is accomplished by baking the valve portion 20 at between 150 C and 170 C, preferably 160 C, for between 5 and 20 minutes, preferably between 9 and 11 minutes.

The valve portion 20 now has a plug 76 which is strong enough to prevent the silicone dispersion from entering the inner chamber 72 when the valve portion 20 is fully dipped into the dispersion. At 150, the balloon portion 70 is formed. This entails inverting the valve portion 20 and the mandrel 80, as was done at 130 to form the plug 76, and dipping the entire valve portion 20 into the dispersion, with the exception of the skirt 54, which is contained within the mandrel 80. This is step 152 of FIG. 3.

At 154, the device 10 is removed from the dispersion and the xylene is allowed to evaporate. This evaporation process is preferably accelerated by spinning the mandrel 80 for approximately 15 minutes. At 156, the thickness of the newly formed balloon wall 74 is examined and, if too thin, the decision is made at 158 to dip the device 10 again and spin for another 15 minutes. Preferably, this process is repeated at least two, more preferably three times, in order to build up the balloon wall 74 and also to create a laminar construction in the wall 74, thereby significantly increasing its strength. In the embodiment, the desired wall thickness is 0.009"–011".

Figure 4C:
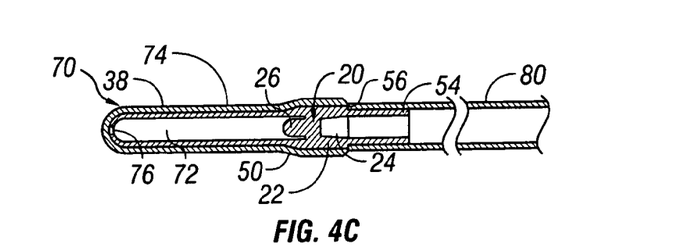

FIG. 4C shows the device 10, attached to the mandrel 80, with a newly formed balloon wall 74 extending over the end portion 40 and back to approximately the ridge 56 where the skirt 54 extends from the valve body 22. Notably, the taper 50 still exists between the upper sidewall 46 and the lower sidewall 48, as the balloon wall 74 closely follows the contours of the valve portion 20.

Having achieved the desired thickness, the device 10 is ready to be fully vulcanized at 160. This is accomplished by baking the device 10 at between 150 C and 170 C, preferably about 160 C, for approximately one hour. Doing so ensures a complete expulsion of the xylene from the wall 74 and the plug 76, thereby leaving a solid device 10 of silicone.

Figure 4D:
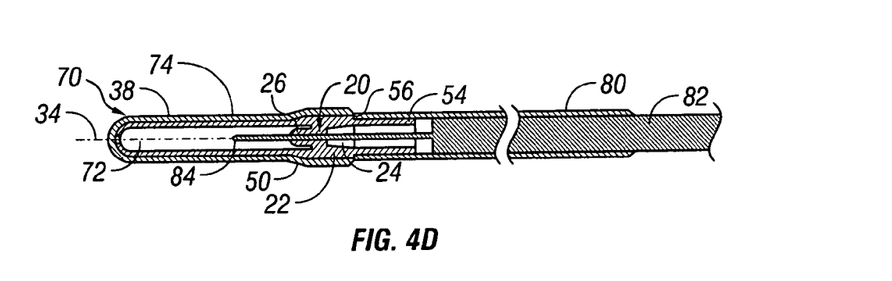

The device 10 must now be pierced, at 170, in order to form piercing 32. Piercing 32 will provide a path for an inflation tube to follow from the inlet 24 to the inner chamber 72. A piercing implement 82 is used having a sharp, needle-like point 84. The piercing implement 82 is inserted through the mandrel 80, which acts as a guide to keep the point 84 substantially travelling along the central axis 34 of the device 10. The implement 82 passes through the mandrel 80, entering the inlet 24 of the device 10, and begins puncturing the valve body 22. The implement continues through the valve body 22 and pierces the valve stem 26, still along the common central axis 34. This is shown in FIG. 4D. For clarity, the piercing 32 shown in FIG. 4D is straight, exiting the valve stem 26 and entering the inner chamber 72 along the central axis 34. However, as discussed above, a bend 36 in the piercing 32, shown in FIGS. 1 and 2, is preferable. As the mandrel 80 limits lateral movement of the implement 82, the bend 36 is formed by manually bending the valve stem 26 to one side prior to completing the piercing operation. Once the valve stem 26 is bent to one side, the implement 82 is pushed through the mandrel 80 until the point 84 exits a side 28 of the valve stem 26. Whether or not a bend 36 is created in the piercing 32, once the point 84 of the implement 82 enters the inner chamber 72, the piercing 32 is complete and the implement 82 is removed from the mandrel 80.

Figure 4E:
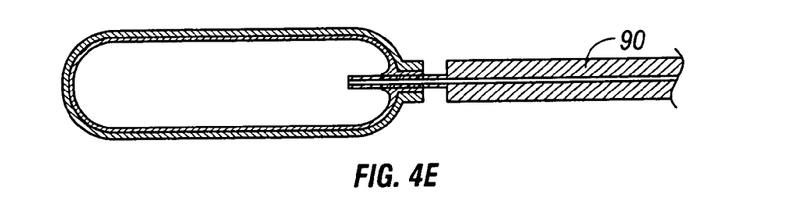
Figure 4F:
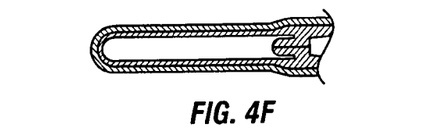

At 180, the device 10 is substantially complete and cut from the mandrel 80. The cut is made along the ridge 56, thereby removing the skirt 54 while leaving the inlet 24 intact. The device 10 is complete but must be tested to ensure that no leaks occur. At 190, an inflation test is performed. As seen in FIG. 4E, an inflation tube 90 is inserted through the newly formed piercing 32. Preferably, this is done manually so as to prevent damage to the valve body 22. The balloon device 10 is then inflated to capacity with a fluid, such as saline or water. The inflation tube 90 is removed and the inflated device 10 is inspected for leaks. Once the fluid-tight integrity of the device 10 has been confirmed, the inflation tube 90 is reinserted and used to deflate the device 10. The inflation tube 90 is again removed. FIG. 4F shows a deflated device 10. Note that the taper 50 is now gone. A degree of hyperplasia occurs during the initial inflation, thereby increasing the deflated diameter of the upper sidewall 46 and the balloon wall 74 thereover. The taper 50 allows for this hyperplasia such that the exterior of the balloon device 10 becomes cylindrical upon completion of the initial inflation at 190. If there is no taper 50, the balloon device 10 would not become cylindrical after the inflation test and would, therefore not fit into transporter tubes, discussed below.

At 200 the balloons are oven dried to remove any remaining test fluid. Preferably the balloons are dried at 90 C for approximately 60 minutes.

Each balloon is then removed from the oven and loaded into a transporter tube at 210. Transporter tubes are the preferred method for packaging and shipping because they are constructed and arranged for use with a linear balloon delivery system such as that disclosed in U.S. patent application Ser. No. 09/547,952, filed Apr. 12, 2000, incorporated by reference herein. The transporter tube is disclosed in U.S. Provisional Patent Application Serial No. (unassigned) filed by the common assignee of the present application on even date herewith and which is also incorporated by reference herein. These transporter tubes are metal tubes which have an inner diameter substantially equal to the outer diameter of the device 10. They allow a physician to load the balloon device 10 into a linear delivery system easily and accurately. They also serve to protect the balloons during shipping and handling.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited in the particular embodiments which have been described in detail therein. Rather, reference should be made to the appended claims as indicative of the scope and content of the present invention.

Additionally, it is understood that terms such as "upper", "lower", "side", "above", "below", and the like, as used herein, are terms of relationship rather than absolute orientation. These relative terms are used to enhance the clarity of description and are in no way limiting or implying that a certain orientation is required to practice the scope of the present invention.

What is claimed is:

1. An implantabic balloon comprising:
    a valve portion having:
        a valve body defining an inlet;
        a valve stem extending from said body opposite said inlet;
        a piercing extending from said inlet, through said body and stem, said valve portion constructed from a soft, elastomeric material having memory thereby causing said piercing to remain closed and fluid-tight unless penetrated by a relatively rigid member, the memory of the material also causing reclosing of said valve to a fluid-tight configuration after the piercing and the withdrawal of the relatively rigid member;
    a balloon portion, integral with said valve portion, constructed and arranged to receive and hold fluids exiting said piercing opposite said inlet.

2. The balloon of claim 1 wherein said valve stem comprises at least one side.

3. The balloon of claim 1 wherein said valve stem comprises a rounded tip.

4. The balloon of claim 1 wherein said valve stem comprises a side and said valve portion further has a sidewall, laterally displaced from said valve stem side, and integral with an inside surface of said balloon portion.

5. The balloon of claim 1 wherein said valve portion is substantially cylindrical.

6. The balloon of claim 1 wherein said valve body, said valve stem, and said inlet are substantially cylindrical and substantially concentric.

7. The balloon of claim 1 wherein said valve stem comprises at least one side and said piercing extends through said side of said stem.

8. The balloon of claim 1 wherein said valve stem comprises a side and said valve portion further has a sidewall extending from said valve body, laterally displaced from said valve stem side.

9. The balloon of claim 8 wherein said valve body forms a curved web, integrally connecting said valve portion sidewall with said valve stem side, said curved web being concave and opening toward said balloon portion.

10. The balloon of claim 1 wherein said soft, elastomeric material comprises silicone.

11. A self-sealing medical balloon of unitary construction, implantable in a human body, comprising:
    a cylindrical valve body having a predetermined diameter and an upper side and a lower side;
    an inlet defined by said valve body lower side;
    a cylindrical valve stem extending upwardly from said valve body, said valve stem having a diameter smaller than said valve body diameter;
    a balloon wall adapted to receive and bold fluids, the balloon wall extending outwardly from said valve body, said balloon wall having an inner diameter, while in a deflated state, which is larger than said valve stem diameter such that an annular space exists between said balloon wall and said valve stem while said balloon is deflated, said annular space provided to relieve stress from a union of said balloon wall and said valve body when said balloon is inflated;
    a piercing extending from said inlet, through said valve body and through said valve stem, into an inner chamber defined by said balloon, said piercing constructed and arranged to remain closed unless a substantially rigid member is pushed through said piercing, such as to inflate said balloon,
    whereby said piercing member recloses after said member is withdrawn, thereby preventing a fluid from escaping from said inner chamber.

12. The balloon of claim 11 whereby said inlet, said valve body, and said valve are substantially concentric, sharing a common longitudinal axis.

13. The balloon of claim 12 whereby said piercing follows said longitudinal axis.

14. The balloon of claim 12 whereby said piercing comprises a curved portion.

15. The balloon of claim 12 whereby said piercing comprises a straight portion and a curved portion, said straight portion extending upwardly from said inlet and substantially parallel to said axis, said curved portion extending from said straight portion to a side of said valve stem.

16. The balloon of claim 11 wherein said annular space is defined on a lower side by a curved web which is concave and opening upwardly.

17. The balloon of claim 11 wherein said balloon is constructed entirely of silicone.

18. The balloon of claim 11 further comprising a removable skirt extending downwardly from said valve body, said skirt providing a surface which may be handled during a balloon manufacturing operation without damaging said balloon wall, or said valve body.

19. The balloon of claim 18 wherein said removable skirt has an outside diameter smaller than an outside diameter of said valve body such that a ridge is formed between said valve body and said skin.

20. A valve of unitary construction, useable to prevent fluid from escaping from an implantable balloon operably attached to the valve, the valve comprising:
   a substantially cylindrical body defining an inlet, concentric with said body, opening in a direction opposite the balloon;
   a valve stem, integral with said body, having a substantially cylindrical side and rounded tip opposite said body and leading to an interior of the balloon;
   a piercing, defined by said valve body and said valve stem, extending from said inlet toward said balloon and leading to the interior of the balloon, said piercing having a bend which curves toward said stem side;
   a cylindrical sidewall, integral with said body, extending in a direction toward said balloon, radially displaced from said stem side, thereby creating an annular space between said stem and said sidewall, said sidewall having an external surface attachable to said balloon.

21. The valve of claim 20 wherein said body further defines a curved portion, concave so as to open toward said balloon interior, connecting said sidewall with said stem.

22. The valve of claim 20 farther comprising an end portion, integral with and extending from said sidewall, which curves inwardly to define an opening having an inner diameter which is smaller than an inner diameter of said cylindrical sidewall.

23. The valve of claim 20 wherein said cylindrical wail comprises a lower sidewall and an upper sidewall and a taper connecting said lower sidewall and said upper sidewall, whereby said lower sidewall has a larger outside diameter than an outside diameter of said upper sidewall.

24. The valve of claim 23 wherein said upper sidewall and said lower sidewall have substantially equal inner diameters.

25. The valve of claim 20 further comprising a skirt extending from said body in a direction opposite said balloon.

26. The valve of claim 25 wherein said skirt has an outer diameter smaller tan an outer diameter of said valve body, thereby providing a visual and tactile definition of an extent of said skirt, such that said skirt may be removed without removing material from said valve body.

27. The valve of claim 25 wherein said skirt is sized to frictionally fit within an open end of a dipping tube.

28. The valve of claim 20 wherein said valve is unitarily constructed from an elastomeric material.

29. The valve of claim 28 wherein said valve is unitarily constructed from silicone.

* * * * *

UNITED STATES PATENT AND TRADEMARK OFFICE
CERTIFICATE OF CORRECTION

PATENT NO.         : 7,160,325 B2
APPLICATION NO. : 09/872704
DATED              : January 9, 2007
INVENTOR(S)        : Randy L. Morningstar It is certified that error appears in the above-identified patent and that said Letters Patent is hereby corrected as shown below:

Column 4, line 30, "e.g. FIGS. 4C and 4D)" should be --(e.g. FIG.'s 4B, 4C and 4D)--.
Column 10, line 25, "tan" should be --than--.

Signed and Sealed this

Twenty-sixth Day of August, 2008

JON W. DUDAS
*Director of the United States Patent and Trademark Office*